United States Patent [19]

Omata

[11] 4,361,948
[45] Dec. 7, 1982

[54] METHOD OF MANUFACTURING CYTODIAGNOSTIC BRUSH ASSEMBLY

[75] Inventor: Katumi Omata, Sagamihara, Japan

[73] Assignee: Olympus Optical Company Ltd., Japan

[21] Appl. No.: 157,096

[22] Filed: Jun. 6, 1980

[30] Foreign Application Priority Data

Jul. 20, 1979 [JP] Japan .................................. 54/92363

[51] Int. Cl.³ ...................... B21D 39/00; B23P 11/00
[52] U.S. Cl. .................................... 29/517; 128/756; 300/21
[58] Field of Search .......................... 29/517; 128/756; 300/21

[56] References Cited

U.S. PATENT DOCUMENTS

| | | | |
|---|---|---|---|
| 2,192,914 | 3/1940 | Ice | 29/517 UX |
| 2,813,442 | 11/1957 | Wingate | 29/517 UX |
| 2,832,118 | 4/1958 | Ehmann | 29/517 X |
| 2,955,591 | 10/1960 | MacLean | 128/756 |
| 2,962,782 | 12/1960 | Beach | 29/517 UX |
| 3,407,477 | 10/1968 | Sahm | 29/517 |
| 4,235,245 | 11/1980 | Naito | 128/756 |

Primary Examiner—Charlie T. Moon
Attorney, Agent, or Firm—Ostrolenk, Faber, Gerb & Soffen

[57] ABSTRACT

A method of manufacturing a cytodiagnostic brush assembly comprises forming a sleeve, which is used to cover and fix the end of a strand or strands which form a brush, by a drawing operation, whereby the sleeve is secured to the strands.

6 Claims, 11 Drawing Figures

FIG. 6
FIG. 5
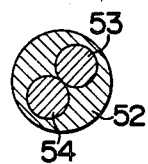
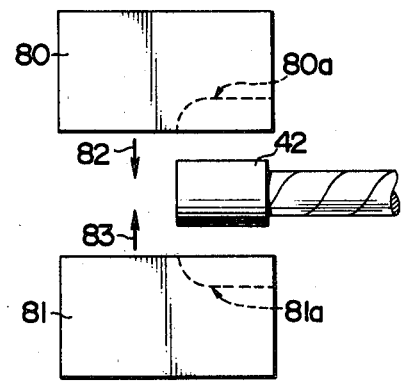
FIG. 7(a)    FIG. 7(b)
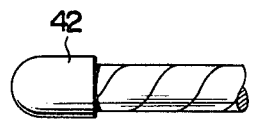    

METHOD OF MANUFACTURING CYTODIAGNOSTIC BRUSH ASSEMBLY

BACKGROUND OF THE INVENTION

The invention relates to a method of manufacturing a cytodiagnostic brush assembly which may be utilized to recover cells from an affected part of a coeliac cavity by being passed through a portion of an endoscope which is adapted to be inserted in such cavity.

FIG. 1 illustrates a cytodiagnostic brush assembly 10 which is used with an endoscope 1. The endoscope 1 includes a portion 5 which is adapted to be inserted into a coeliac cavity and which is provided with a channel 8 for allowing passage of a treatment instrument therethrough. The cytodiagnostic brush assembly 10 is passed through the channel in use. Specifically, the endoscope 1 includes the portion 5 which is adapted to be inserted into a coeliac cavity, an operating end 6 located outside a physical body, an eyepiece assembly 7, and a riser member 9. The portion 5 includes a distal end 2, the bendable portion 3 and a flexible portion 4, all of which are formed of a flexible tubular member, and the riser member 9 is disposed in the distal end 2 to control the direction in which a treatment instrument is caused to project out of the distal end. The cytodiagnostic brush assembly 10 includes an operating wire 10a which extends through a resilient flexible tube 81 formed by a close pitch coil. The entire assembly is detachably mounted in the endoscope 1 by being passed through the channel 8. The cytodiagnostic brush assembly 10 includes a brush 10b formed at the free end of the operating wire 10a which projects out of the resilient flexible tube 81 so as to be directed into a coeliac cavity from the distal end 2 of the endoscope. The brush 10b is in the form of an oblong ring body along which a number of bristles 11 are attached for allowing the recovery of cells from the coeliac cavity.

As is well recognized, in use, the endoscope 1 is inserted into a coeliac cavity such as bronchus, stomach or colon for purpose of observation and diagnosis of an affected part therein. While not shown, it should be noted that the distal end 2 of the portion 5 of the endoscope is provided with an observation window and an illumination window. To facilitate the insertion of the portion 5 into a coeliac cavity and to facilitate the observation and diagnosis of an affected part, the bendale portion 3 can be bent in a controllable manner and the flexible portion 4 is constructed to be a pliable assembly which can be flexed resiliently.

When the portion 5 of the endoscope 1 is inserted into a coeliac cavity with its distal end 2 located opposite to an affected part, the cytodiagnostic brush assembly 10 is driven forward to project the brush 10b out of the distal end 2 to be rubbed against the affected part in order to recover cell tissues thereof. The cytodiagnostic brush assembly 10 with recovered cell tissues is withdrawn, together with the resilient flexible tube 81, through the channel 8 to be taken out of the endoscope.

FIG. 2a shows a conventional construction of the cytodiagnostic brush assembly 10. As shown, it comprises an operating wire 10a extending straight forward and formed by twisting a pair of resilient strands together. A brush 10b, which is connected to the free end of the operating wire 10a, is formed by the pair of resilient strands which are shaped into an oblong ring with a number of bristles 11, of a material such as nylon, held between the strands so as to form a tortoise-shaped scrubbing brush. A short sleeve 12 clamps the free end of the strands forming the brush 10b together with the end of the operating wire 10a. Solder 13 is then injected into the clearance between the sleeve 12 and the operating wire 10a, between the sleeve 12 and the strands of the brush 10b, and between the operating wire 10a and the brush 10b. The solder 13 is shaped into a smooth profile to avoid the formation of any burr which may damage the internal wall of the coeliac cavity or the channel 8.

FIG. 2b shows another cytodiagnostic brush assembly 20 including a brush 20b which is formed by a pair of resilient strands twisted with bristles 21 held therebetween. A sleeve 22 is fitted over the free end of the strands of the brush 20b to cover and fix them, with solder 23 applied thereto and formed to present a smooth profile. The opposite end of the brush 20b is integrally formed with the straight operating wire 20a.

The cytodiagnostic brush assembly 10 or 20 thus formed may be used in the endoscope shown in FIG. 1 to project out of the flexible tube 81 so that the brush 10b or 20b may be used to recover cell tissues from an affected part of a coeliac cavity. The operating wire 10a or 20a of the cytodiagnostic brush assembly 10 or 20 extends through the flexible tube 81 and through the channel 8. The foremost portion of the wire is pliably bent by the riser member 9. It is formed of a hard, resilient strand material so that it may be strongly pulled in order to pass it through the flexible tube 81 formed by a close pitch coil or to operate the brush 10b or 20b without causing a permanent deformation of the wire.

In the construction of the conventional cytodiagnostic brush assemblies 10, 20 shown in FIGS. 2a and b, the sleeve 12 or 22 is fitted over the free end of the strands which define the brush, and solder applied thereto in order to cover and hold them in place. The solder must be formed or finished so as to present a smooth profile. Since the location where the solder is applied to the sleeve 12 or 22 is close to the bristles 11, 21, these bristles may be burned under heat from the soldering iron. Skill and an increased length of working time are required to prevent the bristles from being burned. To give a smooth profile to the solder, a special finishing operation must be performed, and the flux must be removed.

SUMMARY OF THE INVENTION

It is an object of the invention to provide a method of manufacturing a cytodiagnostic brush assembly which eliminates the described disadvantages of the prior art by using a sleeve which is applied to the free end of strands which form a brush of the cytodiagnostic brush assembly and which is secured thereto by forming it by a deforming operation.

In accordance with the invention, the use of solder to cover and secure a sleeve or a blind sleeve to the end of strands which form a brush of a cytodiagnostic brush assembly is avoided, whereby the heat from a soldering iron cannot cause to be burned the bristles of the assembly. Accordingly, the need for a soldering skill is eliminated, and the working time can be substantially reduced. Since the soldering step is eliminated and a finishing step such as removal of a flux from the solder is dispensed with, the manufacturing cost can be reduced.

BRIEF DESCRIPTION OF THE DRAWINGS

FIG. 5 is an enlarged cross section of a sleeve which is secured in place by the method of the invention;

FIG. 6 is a side elevation of deforming equipment used in the method of the invention; and FIGS. 7a and b are a front view and a side elevation of a sleeve applied to a cytodiagnostic brush which is formed by the method illustrated in FIG. 6.

DESCRIPTION OF PREFERRED EMBODIMENTS

Figure 1:
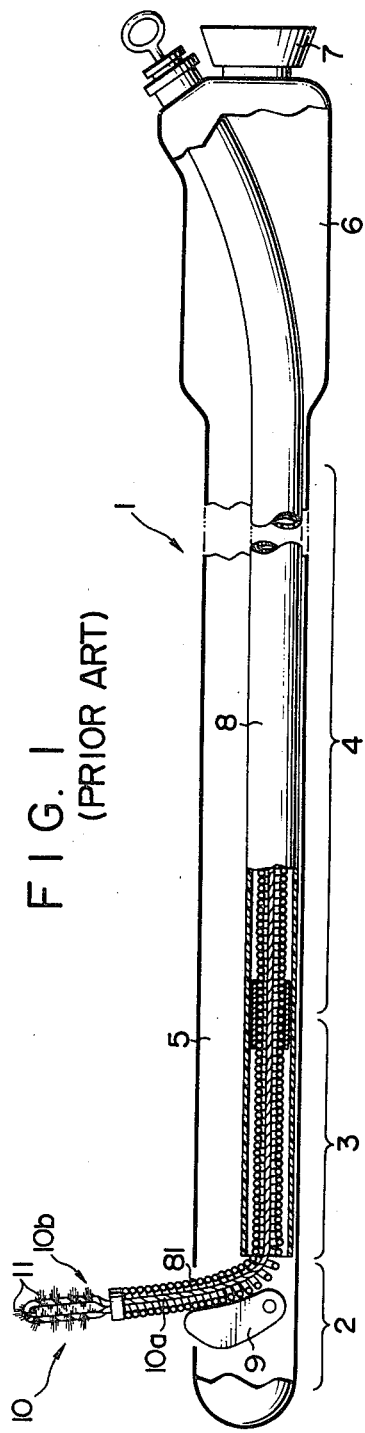
FIG. 1 is a front view, partly broken away, of a conventional endoscope and a cytodiagnostic brush assembly used therein.
Figure 2A:
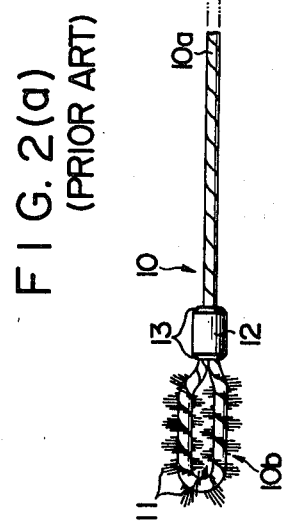
FIGS. 2a and b are enlarged front views of conventional cytodiagnostic brush assemblies.
Figure 2B:
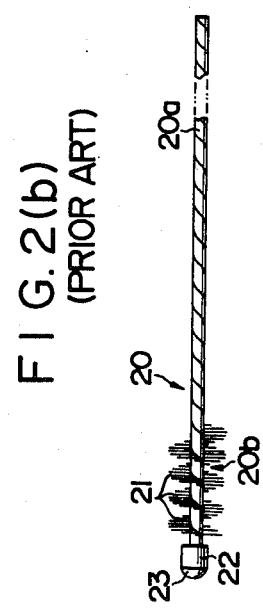
Figure 3A:
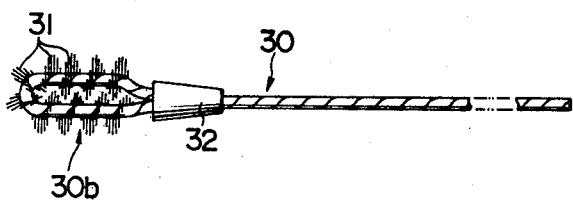
FIGS. 3a and b are enlarged front views of cytodiagnostic brush assemblies manufactured according to the method of the invention.

Referring to FIGS. 3a and b, there are shown cytodiagnostic brush assemblies 30, 40 having sleeves 32, 42, which are applied thereto and formed in accordance with the method of the invention. In accordance with the invention, these sleeves 32, 40 are formed by a deforming operation, thus dispensing with the need to solder them in place. Hence, there is no possibility that the bristles 31, 41 of the brushes 30b, 40b may be burned by heat from a soldering iron as experienced in the prior art. Simultaneously, the need for a soldering skill is eliminated, and the working time can be substantially reduced. It is also unnecessary to form the soldered portion into a smooth profile, resulting in a reduced manufacturing cost.

Figure 3B:
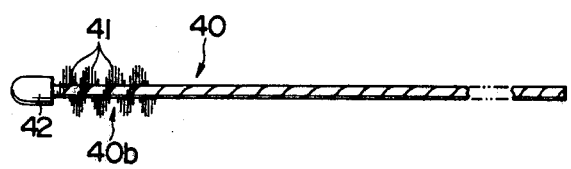
Figure 4A:
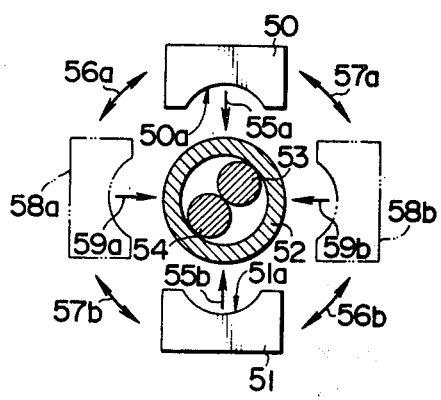
FIGS. 4a and b are an enlarged cross section and a side elevation of deforming equipment which is used in the method of the invention.

FIGS. 4a and b illustrate a deforming equipment which may be used to carry out the method of the invention. In FIG. 4a, deforming equipment which employs drawing dies to secure a sleeve in place is illustrated. Specifically, the equipment includes a pair of vertically spaced dies 50, 51 which are formed with arcuate recesses 50a, 51a formed in their opposing surfaces. A sleeve 52 which is to be applied to the strands of the cytodiagnostic brush assembly is disposed between the dies 50, 51, with the free end of a strand 53 and the opposite end of another strand 54, both of which are used to form a brush 30b (FIG. 3), disposed in juxtaposed relationship within the sleeve 52. The dies 50, 51 are then driven in directions indicated by arrows 55a, 55b to stake the sleeve 52 by pressing it from the opposite directions vertically. The dies 50, 51 are then returned to their original positions, followed by a rotation thereof in directions indicated by arrows 56a, 56b or arrows 57a, 57b while maintaining the opposing relationship of the recesses 50a, 51a. In this manner, these dies are brought to a position shown by phantom lines 58a, 58b where they have been rotated through 90°, for example. The dies 50, 51 are then driven in directions indicated by arrows 59a, 59b to stake the sleeve 52 again by pressing it from the opposite lateral directions. By repeating such operation to press the sleeve 52 in vertical, lateral and oblique directions by means of the dies 50, 51, the sleeve 52 is staked by a deforming operation, with the consequence that the metal of the sleeve 52 is deformed into a configuration as shown in FIG. 5 where it will be seen that the metal flows into the space between the strands 53, 54 to cover and fix them. It should be understood that a plurality of dies which are greater in number than the pair of dies shown may be used for the purpose of the deforming operation. Also it should be understood that instead of rotating the dies 50, 51 as shown in the embodiment of FIG. 4a, the sleeve 52 may be angularly moved in relation to the dies 50, 51.

Figure 4B:
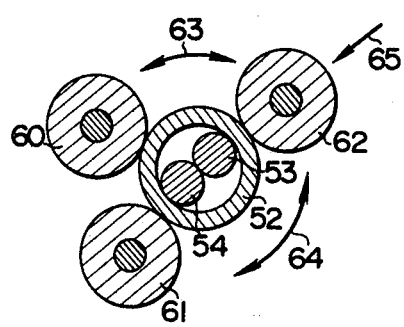

FIG. 4b illustrates deforming equipment which utilizes the principle of operation of a pipe cutter. As before, the opposite ends of strands 53, 54 are inserted into a sleeve 52, which is disposed so that its left-hand side is disposed in abutment against a pair of fixed rollers 60, 61. Another movable roller 62 is disposed to bear against the sleeve 52 on its upper, right-hand peripheral surface. The movable roller 62 is driven toward the center of sleeve 52, in a direction indicated by an arrow 65, while rotating itself and revolving or angularly moving in directions indicated by arrows 63, 64. In this manner, as the movable roller 62 rotates, the sleeve 52 is caused to rotate simultaneously, whereby its entire peripheral surface is uniformly pressed. At the same time, as the movable roller 62 angularly moves, the sleeve is again uniformly pressed from different directions. When the sleeve 52 is uniformly pressed in every direction, it is staked by the deforming operation in the same manner as by the use of the dies shown in FIG. 4a. As a result, the metal of the sleeve 52 flows into space between the strands 53, 54 to cover and fix them, as shown in FIG. 5.

The deforming equipment illustrated in FIGS. 4a and b can be used to stake the sleeves 32, 42 of the cytodiagnostic brush assembly 30, 40 shown in FIGS. 3a and b.

Referring to FIG. 6, there are shown a pair of dies 80, 81, in side elevation, which may be used to shape the sleeve 42 used to cover and fix the free end of the strands of the brush 40b shown in FIG. 3b. The sleeve 42 is secured to the free end of the brush, with its front end being shaped into a rounded form. Accordingly, the opposing surfaces of the dies 80, 81 are formed with recesses 80a, 81a, the front end of each of which is rounded. By placing the sleeve 42 between the recesses 80a, 81a of the dies and driving the dies 80, 81 in directions indicated by arrows 82, 83, the sleeve 42 can be staked into shape as shown in FIGS. 7a and b and secured to the strands, with its forward end rounded.

What is claimed is:

1. A method of manufacturing a cytodiagnostic brush having two wound strands which form the brush, said method comprising the steps of:

providing a cylindrical sleeve having a circular outer diameter and a circular inner diameter and a wall of uniform thickness; said circular inner diameter being sufficiently large so that end portions of said two wound strands may be simultaneously inserted therein;

inserting said end portions of said strands into said sleeve;

securing said sleeve to said strand end portions by deforming said sleeve so as to reduce its said inner and outer diameters, maintain the circular shape of its said outer diameter and provide direct contact between the end portions of both of said strand portions around substantially the entire circumference of each of said strands which lie within said sleeve and said inner diameter of said sleeve along the entire length of said strand portions which lie within said inner diameter of said sleeve.

2. The method of claims 1 in which said securing step comprises a swaging operation.

3. A method according to claim 2 in which said step of securing the sleeve by a swaging operation is performed by using a plurality of dies.

4. The method of claims 1 in which said securing step comprises a rolling operation.

5. The method of claim 4 in which said rolling operation is carried out along the entire length of said sleeve.

6. The method of claim 1 in which said step of securing said sleeve to said strands comprises a cold forming operation.

* * * * *